United States Patent [19]
Paterson

[11] Patent Number: 6,051,237
[45] Date of Patent: *Apr. 18, 2000

[54] SPECIFIC IMMUNOTHERAPY OF CANCER USING A LIVE RECOMBINANT BACTERIAL VACCINE VECTOR

[75] Inventor: Yvonne Paterson, Philadelphia, Pa.

[73] Assignee: The Trustees of the University of Pennsylvania, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/336,372

[22] Filed: Nov. 8, 1994

[51] Int. Cl.[7] .......................... A61K 39/02; A61K 39/38; A61K 39/00; A61K 39/21

[52] U.S. Cl. ..................................... 424/200.1; 424/234.1; 424/277.1; 424/192.1; 424/184.1; 424/207.1

[58] Field of Search ............................. 424/200.1, 234.1, 424/277.1, 192.1, 184.1, 207.1

[56] References Cited

U.S. PATENT DOCUMENTS

| | | |
|---|---|---|
| 4,567,041 | 1/1986 | Likhite . |
| 4,777,239 | 10/1988 | Schoolnik et al. ....................... 530/326 |
| 4,816,253 | 3/1989 | Likhite ....................................... 424/92 |
| 4,879,213 | 11/1989 | Fox et al. ..................................... 435/5 |
| 5,369,008 | 11/1994 | Arlinghause et al. .................. 435/7.23 |
| 5,830,702 | 11/1998 | Portnoy et al. . |
| 5,876,735 | 3/1999 | Reed . |

FOREIGN PATENT DOCUMENTS

| | | |
|---|---|---|
| 63-173594 | 7/1988 | Japan . |
| 9220356 | 11/1992 | WIPO . |
| WO 93/15212 | 8/1993 | WIPO . |

OTHER PUBLICATIONS

Webster's Ninth New Collegiate Dictionary, published by Merriam/Webster Inc. see pp. 782 and 783, 1991.
Bast et al. J. Nat. Cancer Inst. 53(3):757–61 1975 (see abstract).
Silverman et al. Mol. Carcinog 3(6):379–86 1990.
Brasseur et al. Int J. Cancer 52:839–41 1992.
Barry et al. Infection and Immunity 60(4):1625–32 1992.
Cohen, J. Science 262:841–843.
Bowie et al. Science 247:1306–1310 1990.
Kumer et al. PNAS 87:1337–1341 1990.
Aggarwal et al., "Oral Salmonella: Malaria Circumsporozoite Recombinants Induce Specific CD8[+] Cytotoxic T Cells," *J. Exp. Med.* 1990, 172, 1083–1090.
Boon et al., "Tumor Antigens Recognized by T Lymphocytes," *Annu. Rev. Immunol.* 1994, 12, 337–365.
Camilli et al., "Dual Roles of plcA in *Listeria monocytogenes* Pathogenesis," *Mol. Microbiol.* 1993, 8, 143–157.
Cheever et al., "T–Cell Immunity to Oncogenic Proteins Including Mutated RAS and Chimeric BCR–ABL[α]," *Ann. N.Y. Acad. Sci.* 1993, 690:101–112.
Gansbacher et al., "Interleukin 2 Gene Transfer into Tumor Cells Abrogates Tumorigenicity and Induces Protective Immunity," *J. Exp. Med.* 1990, 172, 1217–1224.
Golumbek et al., "Treatment of Established Renal Cancer by Tumor Cells Engineered to Secrete Interleukin–4," *Science* 1991, 254, 713–716.
A. Kruisbeek, *Current Protocols in Immunology*, John Wiley & Sons, Inc., eds., 1994, V.1, 4.1.1–4.1.2.
Restifo et al., "Identification of Human Cancers Deficient in Antigen Processing," *J. Exp. Med.* 1993, 177, 265–272.
Schafer et al., "Induction of Cellular Immune response to a Foreign Antigen by a Recombinant *Listeria monocytogenes* Vaccine," *J. Immunol.* 1992, 149, 53–59.
Stover et al., "New Use of BCG for Recombinant Vaccines," *Nature* 1991, 351, 456–460.
Sun et al., "Isolation of *Listeria monocytogenes* Small–Plaque Mutants Defective for Intracellular Growth and Cell–to–Cell Spread," *Infection and Immunity* 1990, 58, 3770–3778.
Tilney, L.G. et al, "Actin Filaments and the Growth, Movement, and Spread of the Intracellular Bacterial Parasite, *Listeria monocytogenes*," *J. Cell Bio.* 1989 109, 1597–1608.
Townsend et al., "Tumor Rejection after Direct Costimulation of CD8[+] T Cells by B7–Transfected Melanoma Cells," *Science* 1993, 259, 368–370.
Travis, J., "A Stimulating New Approach to Cancer Treatment," *Science* 1993, 259, 310–311.
Wirth, R. et al., "Highly Efficient Protoplast Transformation System for *Streptococcus faecalis* and a New *Escherichia coli–S. faealis* Shuttle Vector," *J. Bacteriol.* 1986, 165, 831–836.
Young, J.F. et al., "Cloning and Expression of Influenza Virus Genes", *The Origin of Pandemic Influenza Viruses*, W.G. Laver, eds., Elsevier Science Publishing Co., Inc., NY, 1983, p. 129.

*Primary Examiner*—Nita Minnifield
*Attorney, Agent, or Firm*—Law Offices of Jane Massey Licata

[57] ABSTRACT

Vaccines containing recombinant *Listeria monocytogenes* capable of expressing tumor specific antigens are provided. These vaccines, when administered to a host, are capable of inducing an immune response to the tumor specific antigen. Methods of using these vaccines in the suppression tumor formation are also provided.

13 Claims, 9 Drawing Sheets

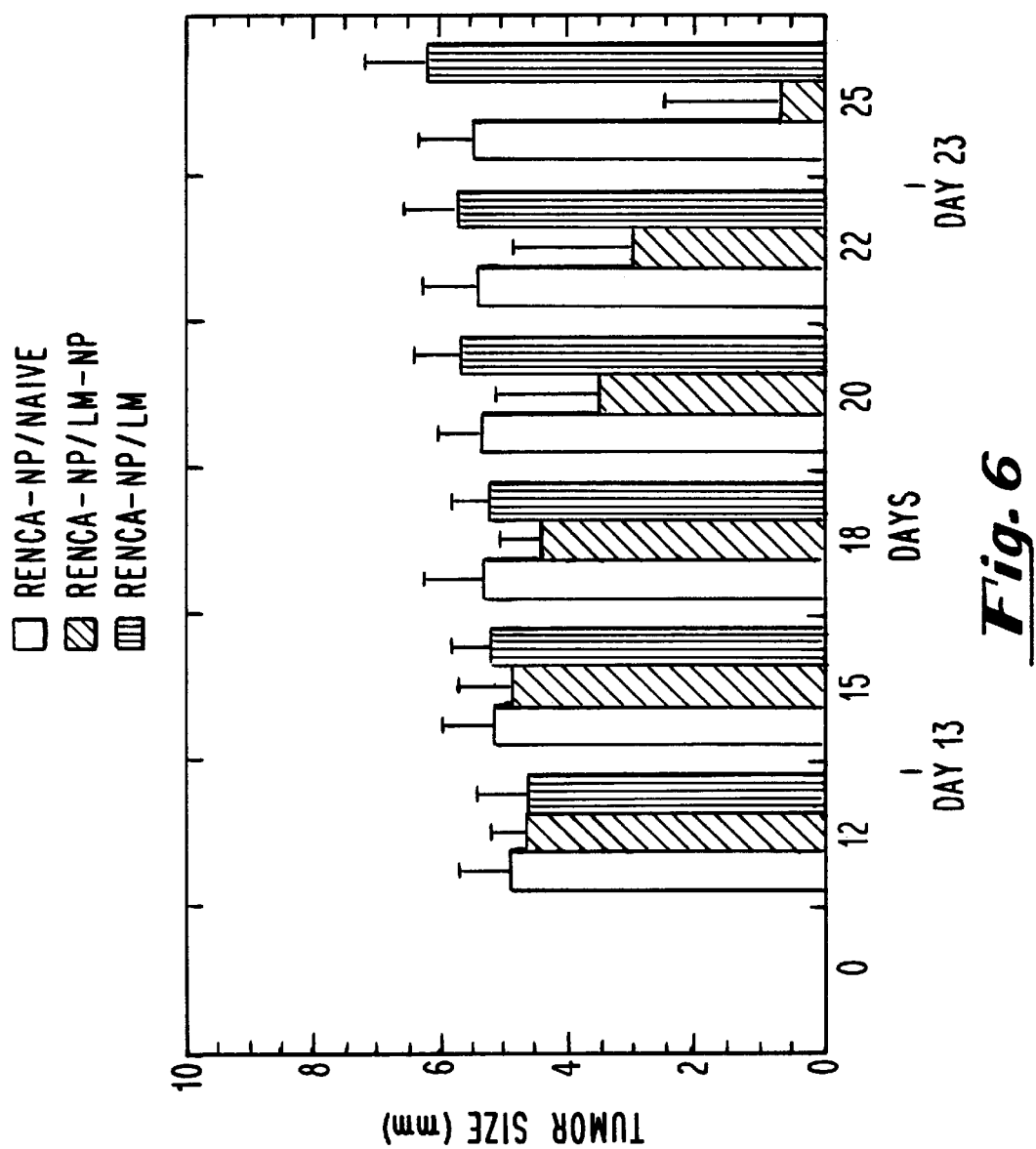

SPECIFIC IMMUNOTHERAPY OF CANCER USING A LIVE RECOMBINANT BACTERIAL VACCINE VECTOR

INTRODUCTION

The invention was made in the course of work supported by the National Cancer Institute. The Government may have certain rights in this invention.

BACKGROUND OF THE INVENTION

Stimulation of an immune response is dependent upon the presence of antigens recognized as foreign by the host immune system. The discovery of the existence of tumor-specific antigens has now raised the possibility of using a host's immune system to intervene in tumor growth. Various mechanisms of harnessing both the humoral and cellular arms of the immune system are currently being explored for cancer immunotherapy.

Elements of the cellular immune response are capable of specifically recognizing and destroying tumor cells. The isolation of cytotoxic T cells (CTC) from tumor-infiltrating cell populations or from peripheral blood suggests that such cells play an important role in natural immune defenses against cancer (Cheever et al., Annals N.Y. Acad. Sci. 1993 690:101–112). CD+8 T cells (TCD8+) in particular, which recognize Class I molecules of the major histocompatibility complex (MHC) -bearing peptides of 8 to 10 residues derived from proteins located in the cytosols, are believed to play an important role in this response. There are now numerous examples of both mouse and human TCD8+ that specifically recognize tumor cells and have therapeutic activity after adoptive transfer, in some cases inducing complete remission. However, despite the potential for T cells to eradicate tumors, it is obvious from the progressive growth of most cancers that many tumors escape recognition by TCD8+ in vivo. The induction of sufficient T cells in vivo has not been very effective. Though a variety of tumors have been found to be immunogenic, stimulation of an effective antitumor immune response has not been found.

One explanation for this phenomena is that tumors may be capable of delivering antigen-specific signals to T cells, but not the costimulatory signals necessary for full activation of T cells. Costimulation of T cells occurs when a surface molecule, B7, on the presenting cells interacts with a T cell molecule known as CD28. It has been observed that T cells receiving the antigen-specific signal (but not B7) become unresponsive. Many tumor cells do not carry the B7 protein, therefore B7 has been added to cancer cells (Travis, J., Science 1993 259, 310–311). It has been demonstrated that expression of the costimulatory ligand B7 on melanoma cells induced the rejection of a murine melanoma in vivo (Townsend, S. E. and Allison, J. P., Science 1993, 259, 368–370). This rejection was found to be mediated by CD8+ T cells; CD4+ T cells were not required. These results suggest that B7 expression may render tumor cells capable of effective antigen presentation, resulting in their eradication in vivo.

The effects of localized secretion of cytokines on tumor progression has also been studied. Secretions of low levels of interleukin-2 (IL-2) in a mouse fibrosarcoma cell line transfected with the human IL-2 gene introduced via a retroviral vector was found to abrogate the tumorigenicity of these cells and induce a long lasting protective immune response against a subsequent challenge with a tumorigenic dose of parent cells (Gansbacher et al., J. Exp. Med. 1990, 172, 1217–1224). In another study, cells from a spontaneously arising murine renal cell tumor were engineered to secrete large doses of interleukin-4 (IL-4) locally (Golumbek et al., Science 1991, 254, 713–716). Animals injected with the tumor cells rejected the IL-4-transfected tumors in a predominantly T cell-independent manner. However, these animals developed a T cell-dependent systemic immunity to the parental tumor. The systemic immunity was tumor-specific and mediated by CD8+ T cells. These experiments suggest that it may be possible to cure parental tumors by generating a systemic immune response by the injection of genetically engineered tumor cells.

There is also evidence to suggest that some tumor cells express low levels of class I molecules in vivo and in vitro. Intracellular antigens must be processed before presentation to CD+8 T cells by major histocompatibility complex (MHC) class I molecules. The antigen processing efficiency of 26 different human tumor lines has been studied (Restifo et al., J. of Exp. Med. 1993, 177, 265–272). Three different cell lines, all human small cell lung carcinoma, consistently failed to process endogenously synthesized proteins for presentation to the T cells. Pulse chase experiments showed that MHC class I molecules were not transported by these cells lines from the endoplasmic reticulum to the cell surface. Northern blot analysis showed that these cells contained little or no mRNA encoding MHC-encoded proteosomes and transporter genes. Treatment with interferon γ enhanced expression of these mRNAs and reversed the observed functional and biochemical deficits. Thus, potential therapeutic applications which include enhancing antigen processing at the level of transcription of MHC-encoded proteosome and transporter genes was suggested.

Immunizing patients with recombinant BCG (bacille Calmette-Guerin) or Salmonella bacteria carrying a gene coding for an antigenic peptide has also been suggested as an oral tumor immunotherapy (Boon et al. Annu. Rev. Immunol. 1994, 12, 337–65). Orally administered live attenuated Salmonella recombinant vaccine, which expressed the full length P. berghei circumsporozite antigen, has been shown to protect mice against malaria. This immune response was mediated by the induction of CD8+ T cells (Aggarwal et al., J. of Exp. Med. 1990, 172, 1083–1090). It is suggested that live attenuated Salmonella recombinants may be useful in the study of other diseases where CTC-mediated immunity may be important, however, no other experiments were reported. BCG has also been implicated as a novel live-vaccine vehicle which may prove useful in stimulating both humoral and cellular immune response to a wide variety of viral, bacterial and protozoal antigens (Stover et al., Nature 1991, 351, 456–460).

It has now been found that the immune response to a tumor-specific antigen can be induced by the administration of a vaccine vector comprising a recombinant form of the intracellular bacterium Listeria monocytogenes which express a tumor specific antigen or fragment thereof. This vaccine vector has been found to be useful in decreasing the size of existing tumors and in inhibiting formation of primary tumors. No other stimulation following antigen presentation was required to induce this response.

SUMMARY OF THE INVENTION

An object of the present invention is to provide a method of inducing an immune response to a tumor-specific antigen in a host having cancer which comprises administering to the host an effective amount of a vaccine comprising a recombinant form of Listeria monocytogenes capable of expressing a tumor specific antigen or fragment thereof.

Another object of the present invention is to provide a use for a vaccine comprising a recombinant form of *Listeria monocytogenes* capable of expressing a tumor specific antigen or fragment thereof to induce an immune response to a tumor specific antigen.

Another object of the present invention is to provide vaccines for the treatment of cancer which comprise a recombinant form of *Listeria monocytogenes* capable of expressing a tumor specific antigen or fragment thereof.

Another object of the present invention is to provide a method of inhibiting the formation of tumors in a host which comprises administering to the host an effective amount of a vaccine comprising a recombinant form of *Listeria monocytogenes* capable of expressing a tumor specific antigen or fragment thereof.

BRIEF DESCRIPTION OF THE DRAWINGS

FIG. 1 provides data from experiments wherein mice in each immunization group were challenged with parental RENCA.

FIG. 2 provides data from experiments wherein mice in each immunization group were challenged with parental CT26.

FIG. 3 provides data from experiments wherein mice from each immunization group were challenged with RENCA transfected with the same NP used to transform the *L. monocytogenes* (RENCA-NP).

FIG. 4 provides data from experiments wherein mice from each immunization group were challenged with CT26 transfected with the same NP used to transform the *L. monocytogenes* (CT26-NP).

FIG. 5 is a bar graph which provides data from experiments wherein it was shown that CTL generated by immunizing Balb/c mice with LM-NP can kill tumor cells CT26 and RENCA that express NP in vitro.

FIG. 6 is a bar graph which provides data from experiments wherein it was shown that immunization by LM-NP causes elimination of RENCA-NP tumor growth.

DETAILED DESCRIPTION OF THE INVENTION

Figure 1:
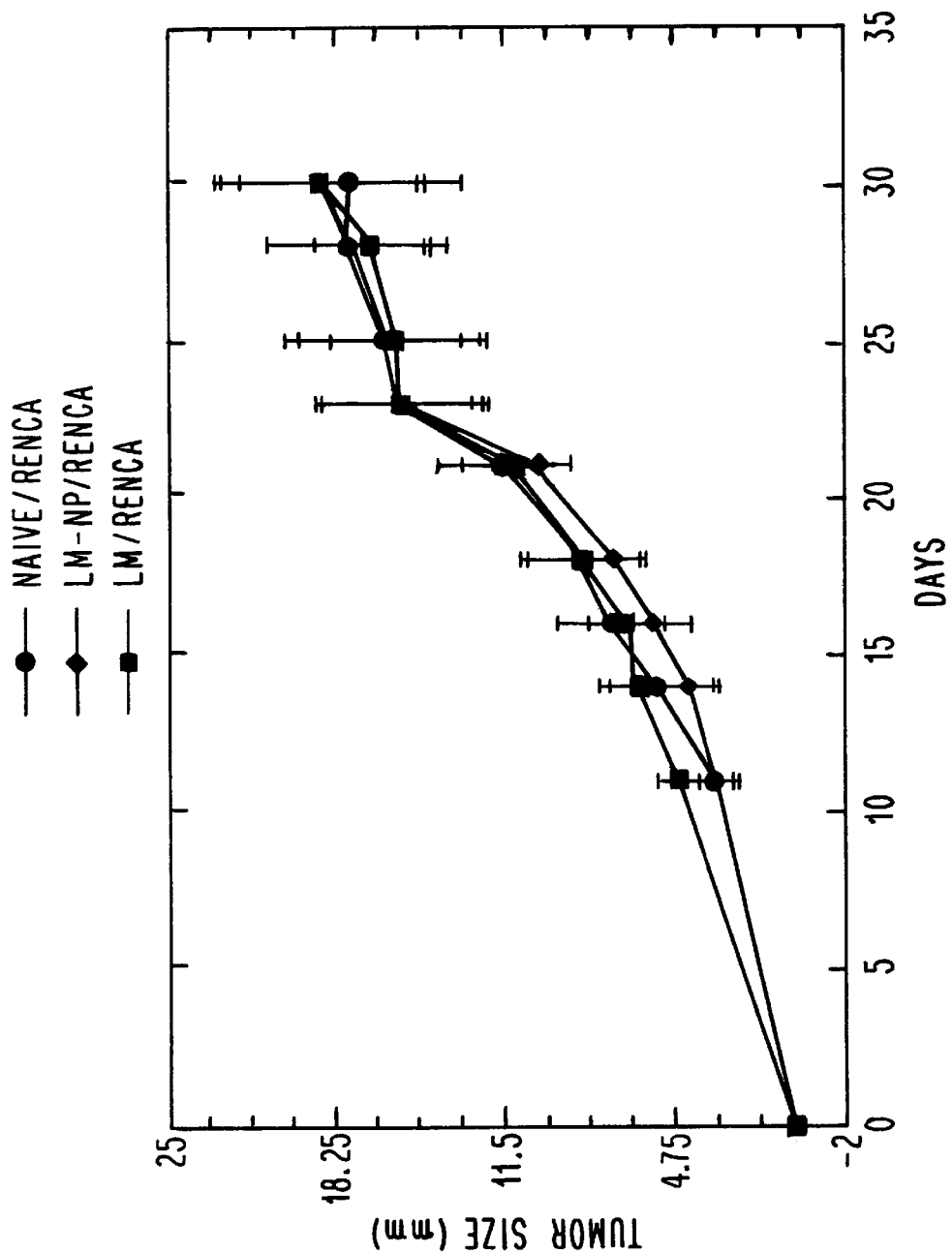
FIGS. 1 through 4 provide line graphs from experiments wherein mice were immunized with either saline (●), *L. monocytogenes* (■), or recombinant *L. monocytogenes* transformed to express influenza nucleoprotein (LM-NP) (♦) and then subsequently challenged with either CT26 or RENCA which had been transfected with the same influenza nucleoprotein (NP) gene that was used to transform the *L. monocytogenes* vector (CT26-NP or RENCA-NP, respectively) or with the parental CT26 or RENCA line.

The immune response to *L. monocytogenes* has been shown to be a TH1, CD4+ T cell and CD8+ T cell response with only very weak humoral responses being engendered. Recombinant forms of the wild-type bacterium have been developed which express the foreign proteins β-galactosidase (Schafer et al., *J. Immunol.* 1992, 149, 53–59), influenza nucleoprotein and HIV gag and nef gene product. Recombinant techniques have been developed to stably integrate these proteins into the Listerial chromosome in such a way that they are secreted by the bacterium. All of these recombinant vectors elicit strong, antigen specific, CTC responses in vivo. Thus, this bacterium serves as an ideal vaccine vector for boosting the CTC response to tumor specific proteins and a unique system to prime the cellular immune response as a vaccine against cancer.

Administration of a live vector such as *L. monocytogenes* results in a long lasting cellular immunity which often cannot be induced with killed preparations or soluble protein and adjuvant. A unique feature of the life-cycle of *L. monocytogenes* is that it invades the host cell and is taken up into a phagosome from which it escapes and then lives and replicates in the cytoplasm. Tilney, L. G. and D. A. Portnoy, *J. Cell Biol.* 1989 109, 1597. Thus, the *L. monocytogenes* vector provides the ability to target foreign proteins and fragments of proteins to the class I MHC restricted pathway. In addition to being a more efficacious vector, *L. monocytogenes*, which is a gram-positive organism, is also much safer than many other live vectors since it is very susceptible to most antibiotics, including penicillin. It also does not have the problems associated with toxicity from endotoxin which gram negative vectors such as Salmonella sp. present. Pre-existing immunity which could prevent effective boosting by a vector which has already been widely used as a vaccine, e.g., Vaccinia or BCG, is not likely to be a problem for *L. monocytogenes*, which has not been used previously in vaccine development. Mutant strains of *L. monocytogenes*, which are avirulent but still protective, are also available for testing as potential vaccine candidates.

Using a model murine system, it has now been found that *L. monocytogenes* can induce an immune response against a protein expressed by tumor cells. This immune response causes the rejection of transferred tumor cells to healthy, immunized mice and effects tumor growth in mice in which tumor growth has already been initiated. See FIGS. 3 through 7.

The ability of a vaccine comprising recombinant *L. monocytogenes* to convey specific protective immunity against the growth of CT26, a mouse colorectal carcinoma tumor and RENCA, a murine renal carcinoma, was examined. In preliminary experiments, *L. monocytogenes* was engineered to secrete nucleoprotein (NP) from A/PR/8/34 as a fusion protein with a major secreted Listerial protein, listeriolysin O (LLO), the product of the hemolysin gene. LLO is normally expressed and secreted in a host vacuole by *L. monocytogenes* and is required for escape of the bacteria into the cytoplasm. The ability of NP secreting *L. monocytogenes* recombinants to target the class I pathway of antigen processing for recognition by bulk influenza specific T cells from three strains of mice was tested. It was determined that the LLO-NP fusion proteins are appropriately processed for presentation by the three MHC class I haplotypes to which the A/PR/8/34 response is restricted, i.e., $K^d$, $D^b$ and $K^k$. Immunization of Balb/c mice with varying doses of LM-NP was demonstrated to result in a strong anti-NP CTC response.

Figure 2:
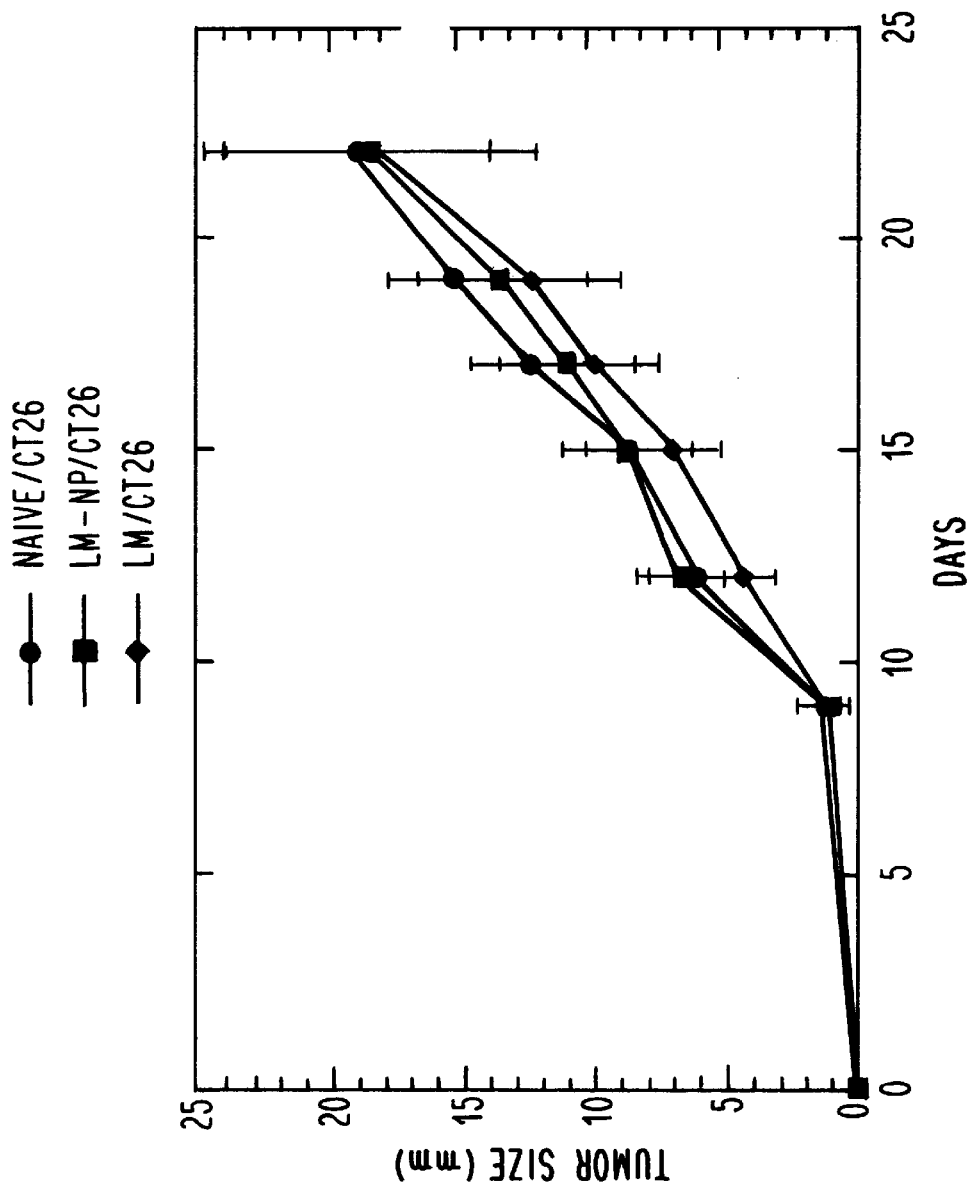
Figure 3:
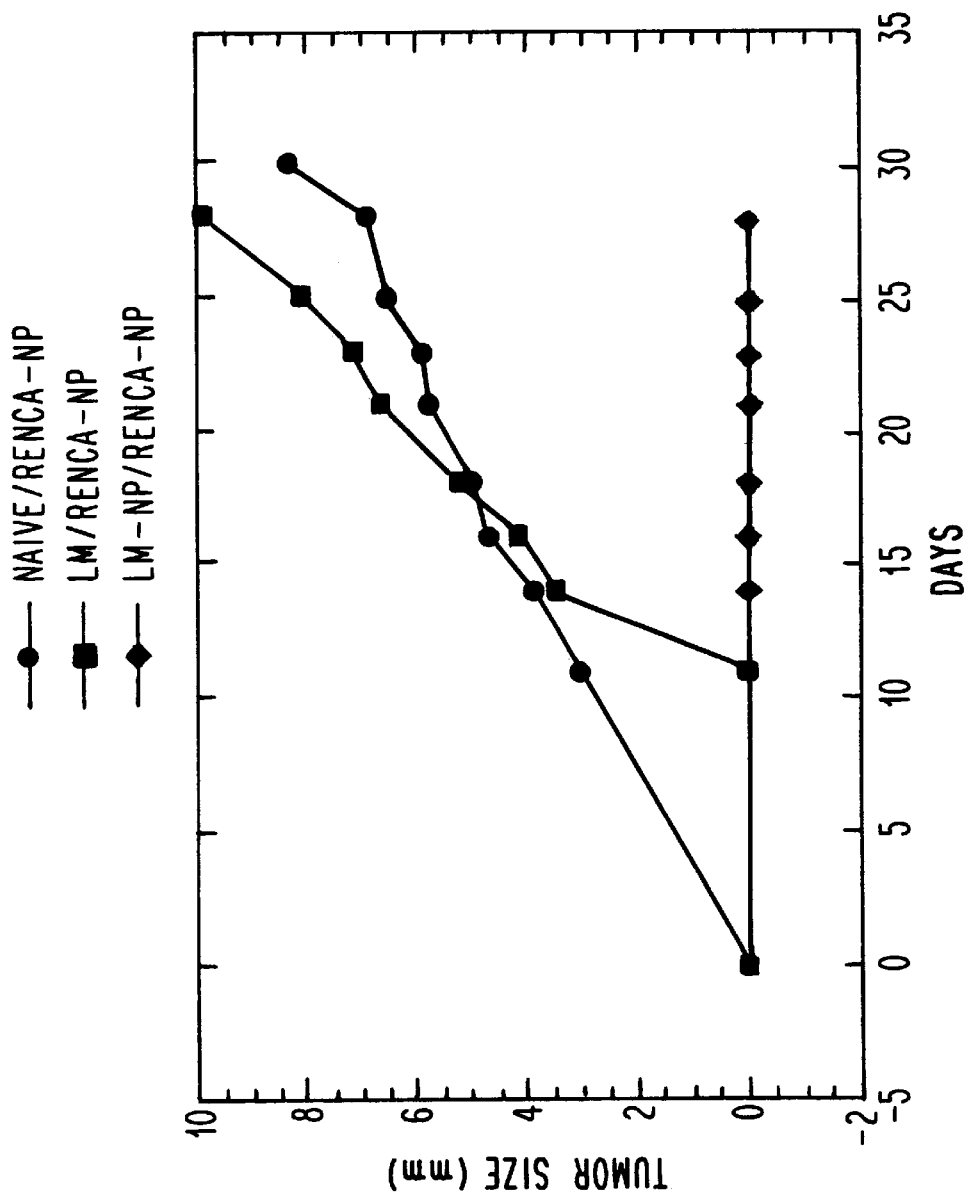
Figure 4:
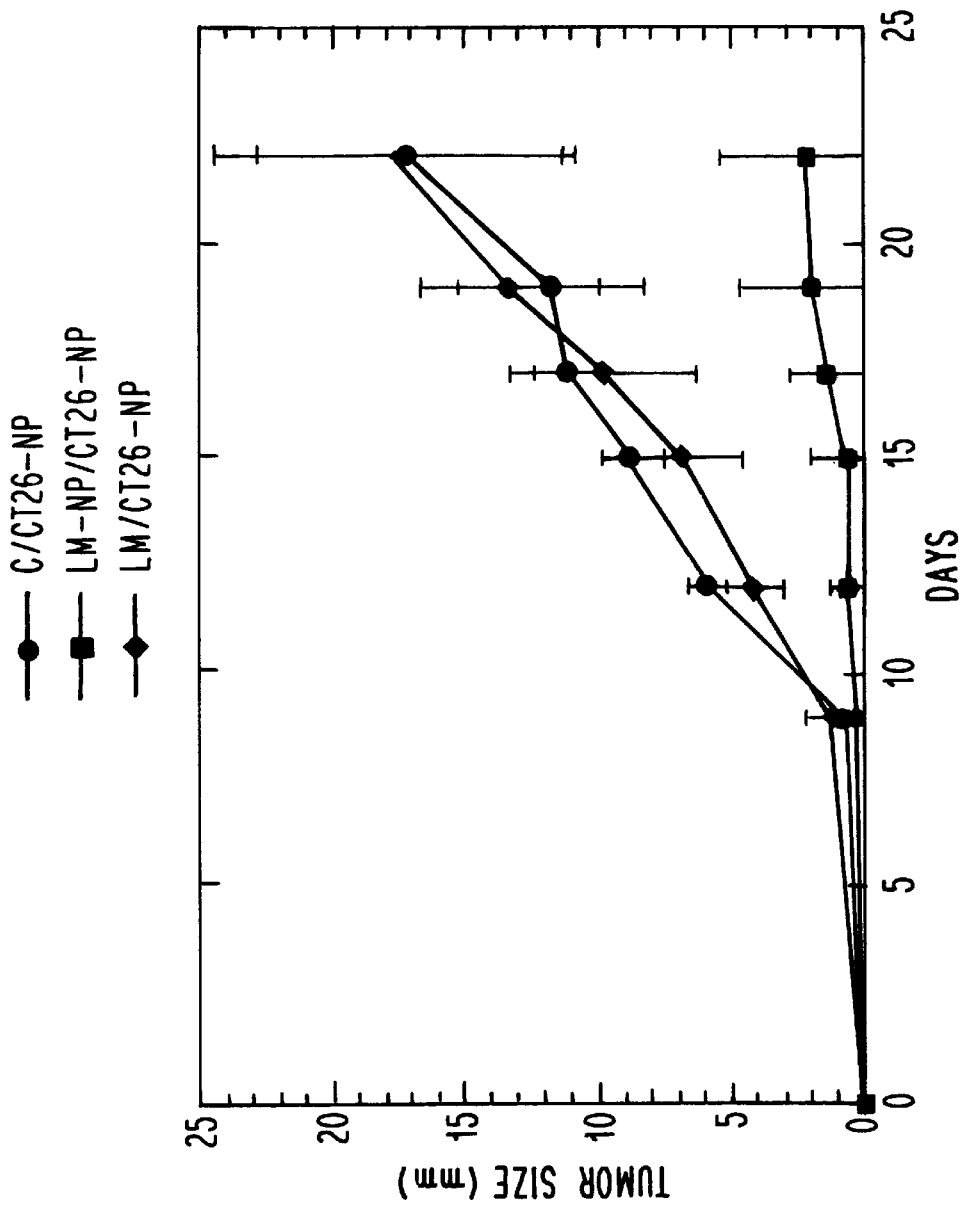

In further experiments, mice were divided into three groups. One group was immunized with one-tenth of an $LD_{50}$ of wild-type *L. monocytogenes*, one group was immunized with sterile saline, and the third group was immunized with a recombinant *L. monocytogenes* vaccine vector which was transformed to secrete influenza nucleoprotein (LM-NP). After two weeks, each group received a similar booster immunization. This immunization schedule was determined to produce strong CTC responses against influenza nucleoprotein. Two weeks after the last immunization, animals in each group were challenged subcutaneously with a tumoricidal dose of either CT26 or RENCA which had been transfected with the same influenza nucleoprotein gene that was used to transform the L. monocytogenes vector (CT26-NP or RENCA-NP, respectively) or with the parental CT26 or RENCA line. Tumor growth was monitored. As shown in FIGS. 3 and 4, animals which received LM-NP as the vaccine and which were challenged with the relevant tumor cell expressing NP were protected from further tumor formation. In the CT26-NP group, after 25 days, 6 of the animals showed no detectable tumor growth, 3 had tumors of less than 5.0 mm and one had a tumor of 9.0 mm (see FIG. 4). In the RENCA-NP group, none of the animals showed any signs of tumor growth (see FIG. 3). In contrast, all the mice in the other groups developed tumors between 1.5 and 3.0 cm (see FIGS. 1 and 2).

Figure 7:
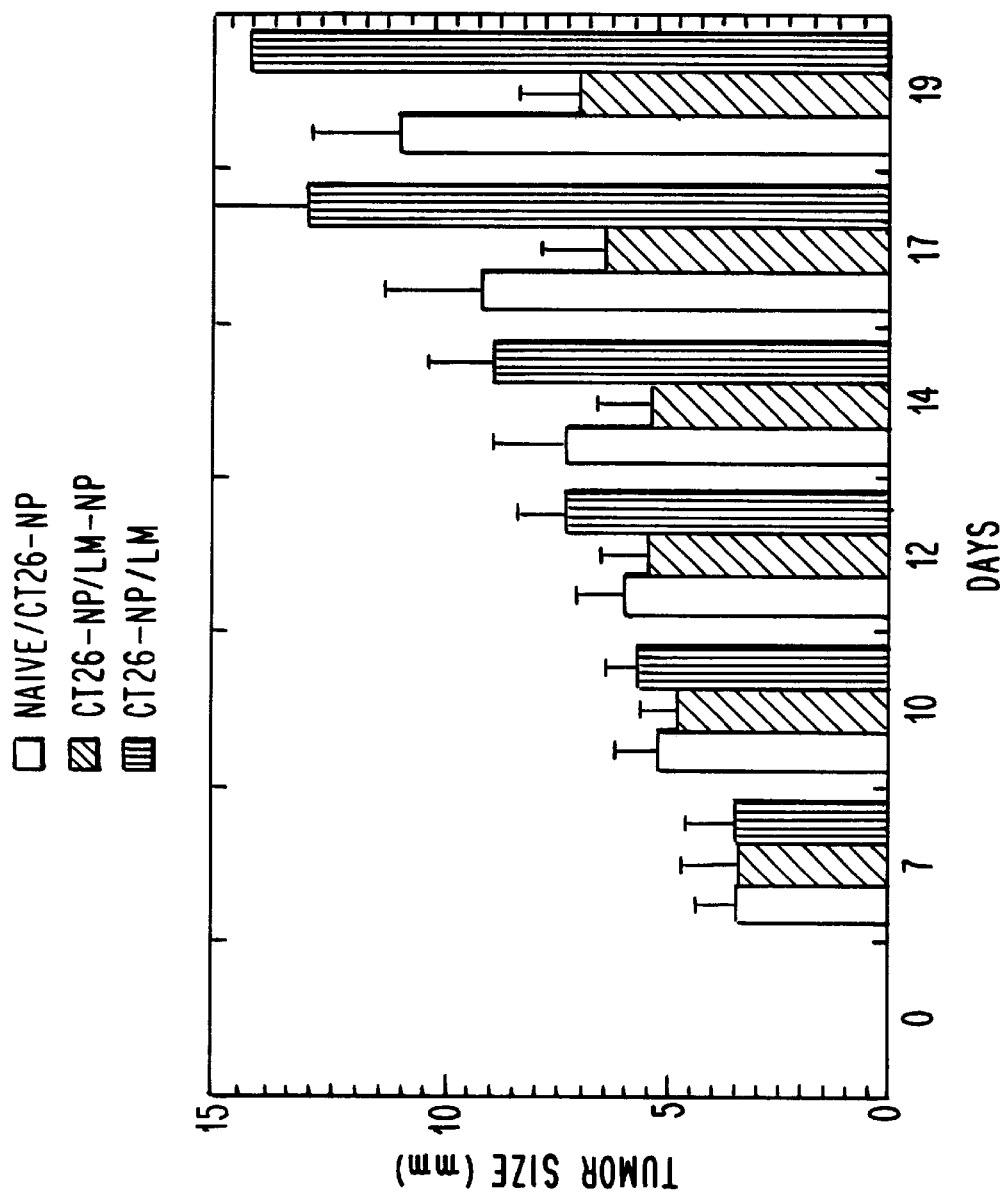
FIG. 7 is a bar graph which provides data from experiments wherein it was shown that immunization by LM-NP causes cessation of CT26-NP tumor growth.

The ability of LM-NP to cause regression and depletion of existing tumors was also demonstrated. Tumor cells (either CT26 or RENCA cells) were introduced subcutaneously into mice. After the formation of measurable tumors, the mice were divided into three separate groups. A first group of mice received LM-NP, a second group of mice received wild type Listeria monocytogenes and a third group of mice received no further treatment. Mice in groups 1 and 2 were given a subsequent booster of either LM-NP or wild type Listeria monocytogenes, respectively. As shown in FIGS. 6 and 7 only the mice that received the LM-NP vaccine showed regression of tumor growth to the point where the tumor was no longer visible.

Vaccines of the present invention require that a tumor specific antigen be known or identified for the cancer. A number of such antigens have been identified. They include the antigen bcr/abl in leukemia, HPVE6 and E7 in the oncogenic virus associated with cervical cancer, MAGE1 and MZ2-E in melanoma, and MVC-1 in breast and pancreatic carcinoma. As will be obvious to those of skill in the art upon this disclosure, however, the invention is applicable to any tumor antigen.

For example, the chronic myeloid leukemia (CML) antigen $p210^{bcr-abl}$, which is expressed in 90 to 95% of CML patients, is a tumor-specific antigen by virtue of its unique junctional sequence. L. monocytogenes recombinants which secrete oligopeptides from the joining region of $p210^{bcr-abl}$ are constructed by any technique which permits the insertion of foreign genes directly into the bacterial chromosome and allows the secretion of the gene product using the LLO signal sequence. The recombinant L. monocytogenes can then be administered as a vaccine, either alone or in the presence of a pharmaceutically suitable carrier, to protect against CML induced by retroviral expression of $p210^{bcr-abl}$. One of skill in the art upon this disclosure could routinely extend this approach to other tumor antigens.

Very stable transformants which secrete a number of large viral proteins have been produced routinely using techniques routine to those of skill in the art. Several techniques for producing recombinant L. monocytogenes are known.

For example, the integration in the Listerial chromosome as a result of a transposon insertion is described by Sun et al., Infection and Immunity 1990, 58, 3770–3778 in the construction of DP-L967. Transposon mutagenesis has the advantage that a stable genomic insertion mutant can be formed but the disadvantage that the position in the genome where the foreign gene has been inserted is unknown.

Cloning of the gene into a prfA-containing vector and using this plasmid to complement a prfA(−) Listeria mutant has been used to construct DP-L2028. DP-L2028 is the influenza NP expressing strain used in the tumor protection experiments.

Several approaches may be taken to express the tumor antigen in Listeria sp. as will be understood by one skilled in the art based upon this disclosure. One example is to generate a fusion protein of the selected tumor antigen and a Listerial protein such as Listeriolysin O or PI-PLC. Another way is through the use of a signal sequence, for a secreted Listerial protein such as hemolysin or phospholipases, employed downstream of a Listerial promoter. The promoters of various L. monocytogenes genes may be used to express foreign antigens. In addition, these genes may be used to generate fusion proteins with foreign antigens. For example, promoters for the genes hly, actA, pica, plcB and mpl, which encode the Listerial proteins hemolysin, actA (a surface protein necessary for host cell actin assembly and essential for cell to cell spread of the bacterium), phosphotidylinositol-specific phospholipase, phospholipase C, and metalloprotease, respectively, can be used.

A more preferred method for producing these recombinants is integration into the Listeria chromosome by homologous recombination with a temperature sensitive plasmid. This method can be used to produce stable transformants that secrete the protein of interest. Unlike the case with transposon mutagenesis, the site of insertion is known. This method allows for the routine insertion of any gene of interest into the chromosome of L. monocytogenes which is then expressed under the control of a L. monocytogenes promoter. One such promoter, the hemolysin promoter, regulates the expression of hly, the Listerial gene which encodes LLO, an abundantly synthesized and secreted protein. It has been shown that the inclusion of the LLO signal sequence allows for the secretion of the expressed protein outside the bacterial cell wall. The construction of these stable recombinants of L. monocytogenes utilizes a region of its chromosome that can act as a site for insertion without disrupting bacterial genes necessary for the growth and spread of the organism (Camilli et al., Mol. Microbiol. 1993, 8, 143–157). This homology region is introduced into the shuttle vector pKSV7, a temperature sensitive plasmid that functions in both E. coli and L. monocytogenes. An EcoR1 site near its center is then used to insert a series of DNA fragments between the two halves of this region. After the addition of a polylinker, the promoter sequence of the Listeria hemolysin gene is inserted. Along with the promoter, downstream sequence information for the first 26 amino acids of the LLO protein (the signal sequence) and four additional amino acids is included to ensure proper processing of the signal sequence. The transcription termination sequence of the hemolysin gene is also included to ensure that stable and regulated synthesis of all transcripts synthesized. These hemolysin regulatory sequences are used to promote the abundant synthesis and secretion of any adjoining downstream gene.

The vaccines of the present invention can be administered to a host, either alone or in combination with a pharmaceutically acceptable carrier, in an effective amount to induce an immune response to a tumor-specific antigen. By "host" it is meant to include any organism capable of sustaining cancerous cells, preferably a human. By "effective amount" it is meant a concentration of recombinant L. monocytogenes capable of expressing a tumor specific antigen which is capable of invoking an immune response in T cells which will eradicate cells containing this antigen. Such amounts can be routinely determined by one of skill in the art upon this disclosure. By "pharmaceutically acceptable carrier" it is meant to include, but is not limited to, sterile distilled water, saline, phosphate buffered solutions or bicarbonate buffered solutions. The pharmaceutically acceptable carrier selected and the amount of carrier used will depend upon the mode of administration. Administration may be oral, parenteral, intranasal, intramuscular, intravascular, intrarectal, intraperitoneal, or any one of a variety of well-known routes of administration. The route of administration may be selected in accordance with different tumors. For example, for treatment of cancers of the alimentary tract, oral administration may be used. For treatment of colorectal cancer, intra-rectal immunization may be used. For the treatment of ovarian or pancreatic cancer, intraperitoneal administration may be used. The vaccines of the present invention may be administered in the form of elixirs, capsules or suspensions for oral administration or in sterile liquids for parenteral or intravascular administration. The vaccines may be stored frozen, at 4° C., at room temperature or lyophilized.

In a preferred embodiment, the vaccines of the present invention are administered to a host either alone or in combination with another cancer therapy to inhibit or suppress the formation of tumors.

Thus, the vaccines of the present invention can be used to protect people at high risk for cancer because of familial genetics or other circumstances that predispose them to certain types of cancer, e.g., cervical cancer in women whose husbands have papilloma virus. In addition, the vaccines can used as a cancer immunotherapy after debulking of tumor growth by surgery, conventional chemotherapy or radiation treatment. Following such treatments, recombinant L. monocytogenes expressing the tumor antigen can be administered. The CTC response to the tumor antigen produced by the vaccine will destroy remaining metastases and prolong remission from the cancer. It is also believed that the vaccines of the present invention can be used to effect the growth of previously established tumors.

The following examples are provided for illustrative purposes only and are not intended to limit the invention.

EXAMPLES

Example 1

A sequence encoding the first 420 amino acids of Listeriolysin O (LLO) and its promoter along with some upstream regulatory sequences was PCR amplified from *L. monocytogenes* chromosomal DNA (wild type strain 10403s) and ligated to PCR amplified DNA encoding NP, derived from plasmid pAPR502. (Young, J. F., U. Desselberger, P. Graves, P. Palese and A. Shatzman, "Cloning and Expression of influenza virus genes", *The Origin of Pandemic Influenza Viruses*, W. G. Laver, eds., Elsevier, New York, 1983, p. 129). The construction resulted in an in-frame fusion plus the addition of two amino acids at the site of the fusion junction. The fusion was cloned into the shuttle plasmid pAM401, a shuttle vector able to replicate in both gram+ and gram− bacteria which contains a gram+ chloramphenicol resistance gene and a gram− tetracycline resistance gene (Wirth, R., F. Y. An and D. B. Clewell, *J. Bacteriol.* 1986, 165, 831). The resultant plasmid, pDP1659, was introduced into wild type *L. monocytogenes* (strain 10403s) by electroporation to yield *L. monocytogenes* strain DP-L1659. This recombinant strain was clearly able to make and secrete a fusion protein of the predicted size (105 kD) as determined by Western blot analysis of the secreted proteins in the culture supernatants using anti-LLO polyclonal antiserum and anti-NP monoclonal antibody. The presence of the fusion gene under the control of the LLO promoter in a multicopy plasmid resulted in reduced secretion of the chromosomally encoded LLO, but not to the extent that it prevented escape of the bacteria from the vacuole or subsequent intracytoplasmic growth. However, this strain was not stable in the absence of chloramphenicol.

To construct *L. monocytogenes* strain, DP-L2028, which is stable in vivo and which was used in Examples 2 through 6, plasmid pDP-1659 was modified by inserting the prfA gene from 10403s and then used to transform a prfA-*L. monocytogenes* mutant DP-L1075. This resulted in *L. monocytogenes* strain DP-L2028 which secretes the LLO-NP fusion protein stably in vivo and in vitro.

Example 2

Treatment of Mice with LM-NP

One hundred and twenty Balb/c mice were divided into three groups of 40. One group was immunized with one-tenth of an LD50 of wild-type *L. monocytogenes*, one group was immunized with sterile saline and the third group was immunized with a recombinant *L. monocytogenes* vaccine vector transformed to secrete influenza nucleoprotein (LM-NP). After two weeks, each group received a similar booster immunization. This immunization schedule was determined to produce strong CTC responses against influenza nucleoprotein. Two weeks after the last immunization, animals in each group were challenged subcutaneously with either CT26 or RENCA which had been transfected with the same influenza nucleoprotein gene that was used to transform the *L. monocytogenes* vector (CT26-NP or RENCA-NP, respectively) or with the parental CT26 or RENCA line. Each mouse was administered $5 \times 10^5$ tumor cells, which is 50 times the tumoricidal dose. Tumor growth was monitored every two days in these six groups of animals. Results from this study are shown in FIGS. 1 through 4. The only group showing any protection from the tumoricidal dose was the animals which received LM-NP as the vaccine and which were challenged with the relevant tumor cell expressing NP. In the CT26-NP group, after 25 days, 6 of the animals showed no detectable tumor growth, 3 had tumors of less than 5.0 mm and one had a tumor of 9.0 mm. In the RENCA-NP group, none of the animals showed any signs of tumor growth. In contrast, all the mice in the other groups have tumors between 1.5 and 3.0 cm.

In order to maintain the foreign NP gene, CT26-NP is usually maintained on the antibiotic G418. It is believed that the small number of CT26-NP tumor cells that grew in the LM-NP immunized mice are cells which have lost the NP gene in the absence of G418.

Example 3

Figure 5A:
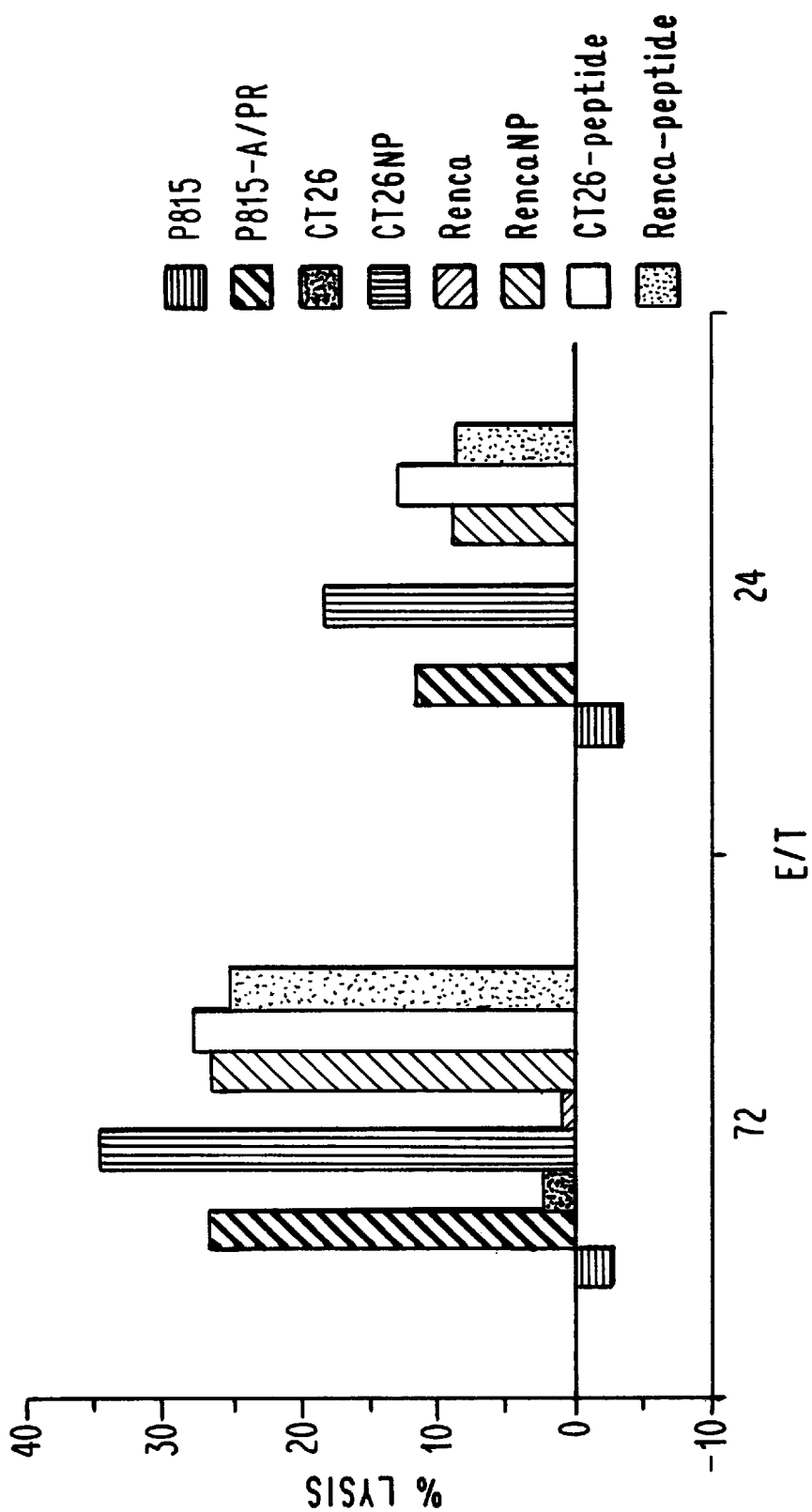
FIG. 5A shows effectors stimulated with A/PR/8.
Figure 5B:
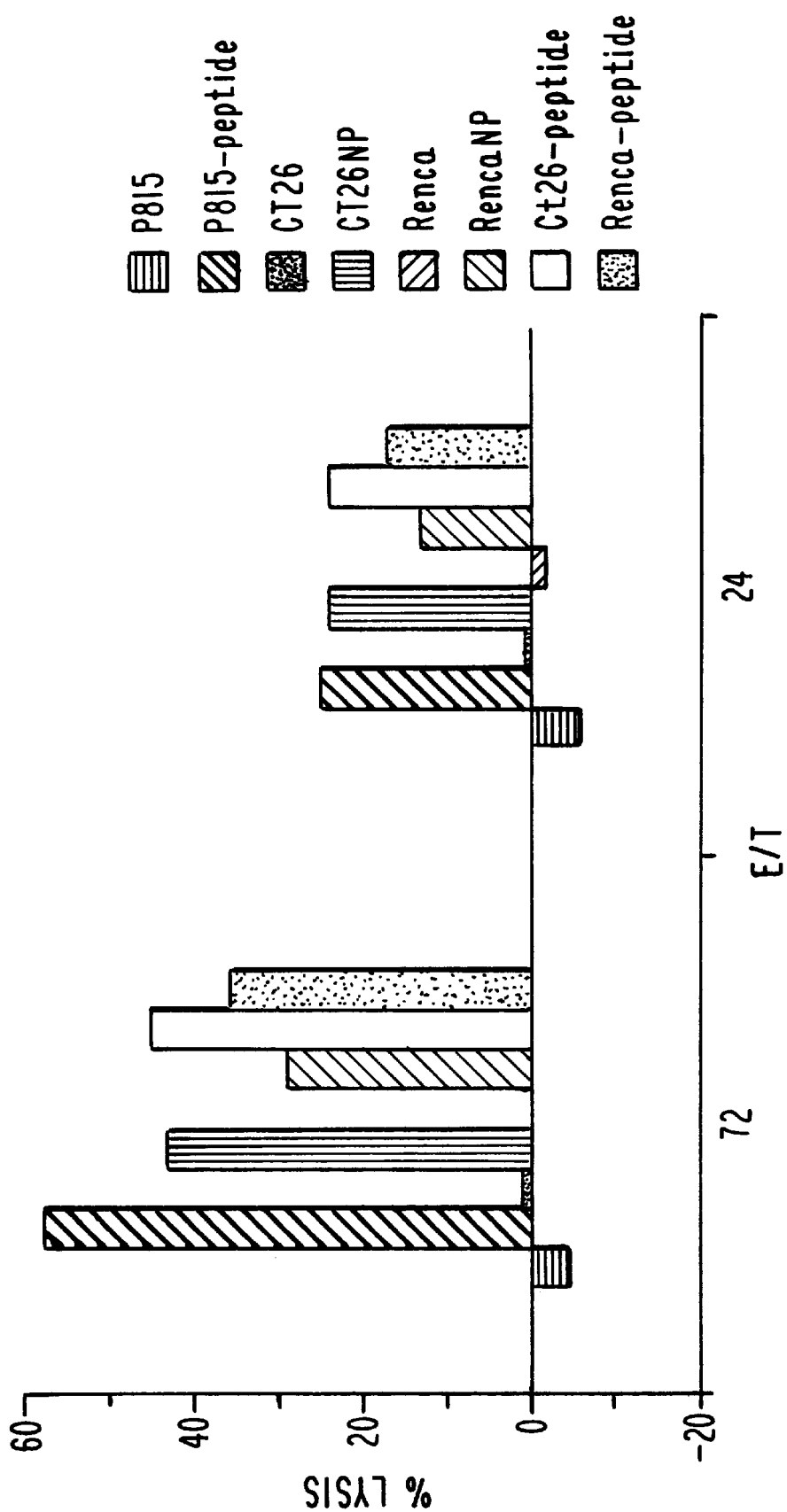
FIG. 5B shows effectors stimulated with peptides.

CTL Generated by Immunizing Balb/c Mice with LM-NP Can Kill Tumor Cells CT26 and RENCA that Express NP In Vitro Mice were immunized with 0.1 $LD_{50}$ of LM-NP. Two weeks later, the mice were sacrificed and primary cultures were set up of spleen cells with either influenza infected (A/PR8/34) splenocytes (FIG. 5A) or with a synthetic peptide 147–158 known to represent the immunodominant epitope of the NP protein (FIG. 5B). After four days in culture, the cytolytic activity of both populations was measured against CT26-NP, RENCA-NP and the parental cell lines CT26 and RENCA. A positive control was included (P815, a mastocytoma tumor cell line known to be efficiently lysed by H-$2^d$ restricted CTL in the presence of the peptide or when infected by A/PR8/34). As FIG. 5A shows, RENCA-NP and CT26-NP, but not the parental lines, were lysed by NP specific effectors induced by immunizing with LM-NP and expanded with A/PR8/34. In FIG. 5B, a similar experiment in which the effectors were expanded with peptide show similar results.

Example 4

Immunization by LM-NP Will Cause Elimination of RENCA Tumor Growth

In this experiment, immunization with LM-NP after tumor growth had been initiated caused regression and depletion of tumors. Tumor cells ($5 \times 10^5$) were introduced subcutaneously to 30 mice. On Day 13, after measurable tumors (5 mm) had grown in the mice, they were divided into three groups of ten. Ten mice received LM-NP, 10 mice received wild type *Listeria monocytogenes* and ten received no further treatment. On Day 23 the mice were immunized again with either LM-NP or wild type *Listeria monocytogenes*. As FIG. 6 shows, only the mice that received the LM-NP vaccine show regression of tumor growth to the point where the tumor was no longer visible in 9 out of 10 mice.

Example 5

Immunization by LM-NP Will Cause Cessation of CT26-NP Tumor Growth

The experiment described in Example 4 was also done with the colorectal CT26-NP tumor cells. CT26-NP is a much faster growing tumor and is also more unstable in its expression of NP. Nevertheless, in this experiment, it was also found that immunization by LM-NP after tumor growth has been initiated halts tumor growth. Tumor cells ($5 \times 10^5$) were introduced subcutaneously to 30 mice. On Day 10, after measurable tumors (5 mm) had grown in the mice, they were divided into three groups of ten. Ten mice received LM-NP, 10 mice received wild type *Listeria monocytogenes*, and 10 mice received no further treatment. On Day 17 the mice were immunized again with either LM-NP or wild type *Listeria monocytogenes*. As FIG. 7 shows, only the mice that received the LM-NP vaccine show a change in tumor growth. However, unlike the case with RENCA, regression of growth was not observed in as many mice. This may be because by Day 17, instability of the CT26-NP tumor cells resulted in many of the tumor cells losing the NP antigen.

Example 6

Inhibition of Tumor Growth is Caused by CD8+ T Cells

Figure 8:
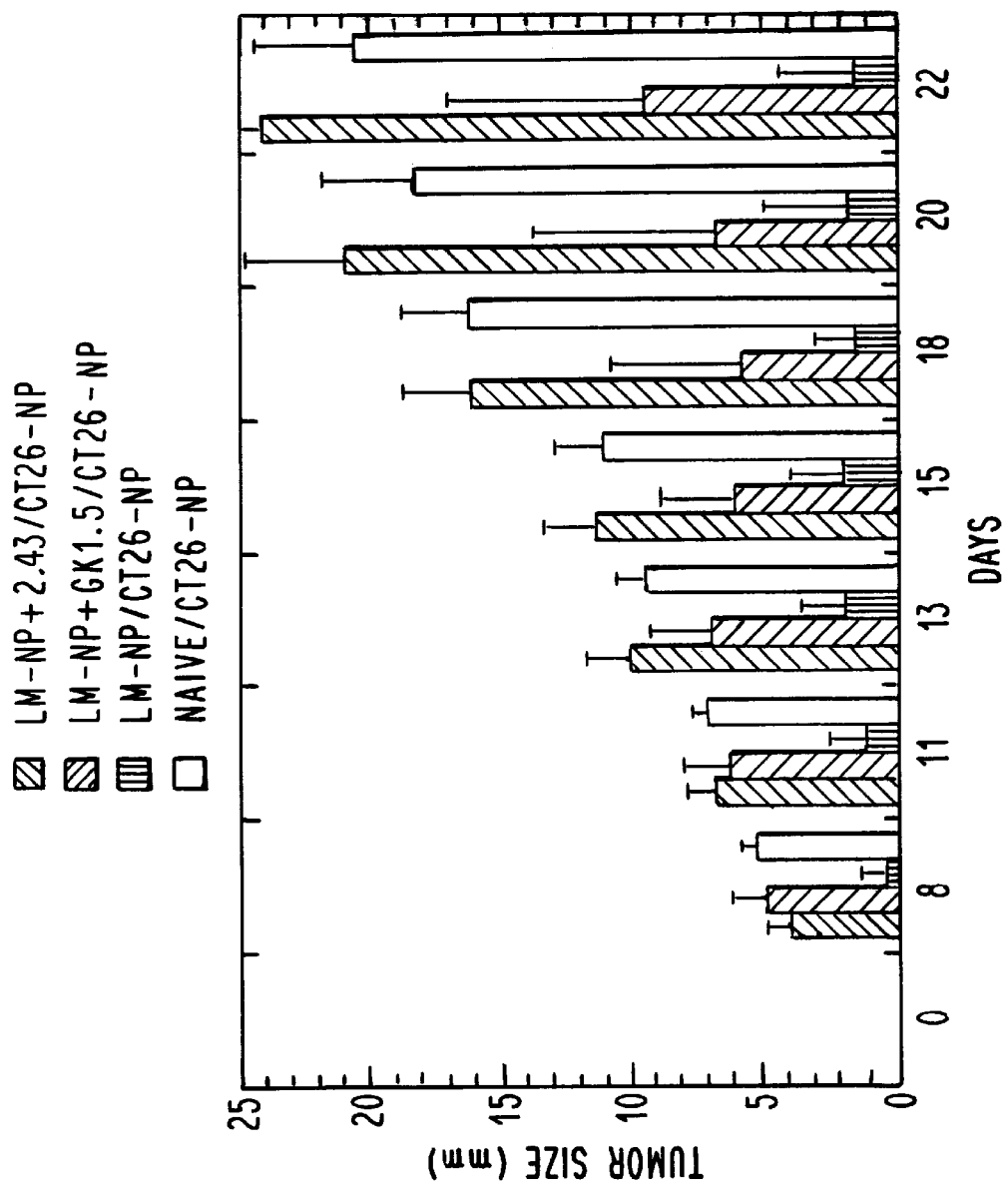
FIG. 8 is a bar graph which provides data from experiments wherein it was shown that inhibition of tumor growth is caused by CD8+ T cells.

In this experiment, 30 mice were immunized with LM-NP using the same protocol as discussed in Example 2. Ten days after the last immunization, 10 mice were depleted of CD8+ cells by immunizing with antibody 2.43 (specific for the CD8 molecule); 10 mice were depleted of CD4+ cells by immunizing with GK 1.5 (specific for the CD4 molecule); and 10 mice were left with a complete T cell repertoire. (The protocol for depletion of CD8+ or CD4+ T cells was that as described by A. Kruisbeek, *Current Protocols In Immunology*, Coligan et al., eds, John Wiley & Sons, Inc., 1994, V.1, 4.1.1–4.1.2). After T cell depletion, the mice were challenged subcutaneously with $5 \times 10^5$ CT26-NP cells per mouse. As a control, 10 naive mice were also challenged with the same dose. As FIG. 8 shows, the group of mice in which the CD8+ T cell subset was depleted showed similar tumor growth to the control (naive) group of mice. The mice in which the CD4+ T cell subset was depleted showed reduced protection against tumor growth, indicating that CD4+ cells play an accessory response in the control of tumor growth; and the mice with a complete T cell repertoire show protection against tumor growth induced by the LM-NP vaccine.

What is claimed is:

1. A method of inducing an immune response to a tumor-specific antigen in a host comprising administering to a host having cancer an effective amount of a vaccine comprising a recombinant form of *Listeria monocytogenes* which grows and spreads and is capable of expressing a tumor specific antigen, wherein said cancer is selected from the group consisting of leukemia, cervical cancer, melanoma, breast cancer and pancreatic cancer.

2. The method of claim 1 wherein said recombinant form of *Listeria monocytogenes* is capable of expressing a tumor specific antigen selected from the group consisting of bcr/abl, HPVE6, E7, MZ2-E, MAGE-1 and MVC-1.

3. The method of claim 1 wherein said vaccine is administered orally.

4. A vaccine for inducing an immune response to a tumor specific antigen comprising a recombinant form of *Listeria monocytogenes* which grows and spreads and is capable of expressing a tumor specific antigen of a cancer selected from the group consisting of leukemia, cervical cancer, melanoma, breast cancer and pancreatic cancer.

5. The vaccine of claim 4 further comprising a pharmaceutically acceptable vehicle.

6. The vaccine of claim 4 wherein said recombinant form of *Listeria monocytogenes* is capable of expressing a tumor specific antigen selected from the group consisting of bcr/abl, HPVE6, E7, MZ2-E, MAGE-1 and MVC-1.

7. A method of suppressing formation of tumors in a host comprising administering to a host an effective amount of a vaccine comprising a recombinant form of *Listeria monocytogenes* which grows and spreads and is capable of expressing a tumor specific antigen of a cancer selected from the group consisting of leukemia, cervical cancer, melanoma, breast cancer and pancreatic cancer.

8. The method of claim 7 wherein the recombinant form of *Listeria monocytogenes* is capable of expressing a tumor specific antigen selected from the group consisting of bcr/abl, HPVE6, E7, MZ2-E, MAGE-1 and MVC-1.

9. The method of claim 8 wherein the tumor is leukemia.

10. The method of claim 8 wherein the tumor is cervical cancer.

11. The method of claim 8 wherein the tumor is melanoma.

12. The method of claim 8 wherein the tumor is breast cancer.

13. The method of claim 8 wherein the tumor is pancreatic cancer.

* * * * *

UNITED STATES PATENT AND TRADEMARK OFFICE
CERTIFICATE OF CORRECTION

PATENT NO. : 6,051,237
DATED : April 18, 2000
INVENTOR(S) : Yvonne Paterson

It is certified that error appears in the above-identified patent and that said Letters Patent is hereby corrected as shown below:

At Col. 6, Line 16, please delete "pica" and insert therefor --plcA--

Signed and Sealed this

Twenty-seventh Day of March, 2001

Attest:

NICHOLAS P. GODICI

*Attesting Officer*   *Acting Director of the United States Patent and Trademark Office*